United States Patent [19]

Szántay et al.

[11] 4,364,931

[45] Dec. 21, 1982

[54] COMPOSITE INSECT ATTRACTANT FOR MALE WHITE-LINE DART MOTHS AND A PROCESS FOR PREPARING THE ACTIVE INGREDIENTS THEREOF

[75] Inventors: Csaba Szántay; Lajos Novàk; Miklós Tóth; Budapest; József Jakab, Gyöngyös; Attila Kis-Tamás, Budapest, István Ujvīria, Budapest; Ferenc Jurák, Budapest, all of Hungary

[73] Assignee: Egyt Gyogyszervegyeszeti Gyar, Budapest, Hungary

[21] Appl. No.: 220,113

[22] Filed: Dec. 24, 1980

[30] Foreign Application Priority Data

Dec. 29, 1979 [HU] Hungary .............................. EE-2721

[51] Int. Cl.³ ............................................. A01N 17/14
[52] U.S. Cl. ..................................................... 424/84
[58] Field of Search ......................................... 424/84

[56] References Cited

PUBLICATIONS

Chemical Abstracts, vol. 94:115930m; vol. 95:56284.
J. Econ. Entomology, vol. 66(1), 1973, pp. 261 and 262.

Primary Examiner—Donald B. Moyer
Attorney, Agent, or Firm—Karl F. Ross

[57] ABSTRACT

The invention relates to a composite insect attractant for male white-line dart moths (*Scotia segetum*) containing 7[Z]-dodecen-1-ol acetate of the formula [I]

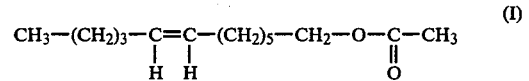

and 9[Z]-tetradecen-1-ol acetate of the formula [II]

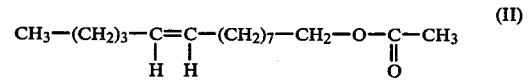

as active agents in a weight ratio of I to II of [50–99]:[50–1], optionally along with a liquid or solid adjuvant.

Another object of the invention is an insect trap containing said composition and a process for attracting and trapping male white-line dart moths as well as a process for disrupting their mating by air permeation technique. The invention relates further to a novel process for the preparation of the active ingredients of the composition.

6 Claims, No Drawings

COMPOSITE INSECT ATTRACTANT FOR MALE WHITE-LINE DART MOTHS AND A PROCESS FOR PREPARING THE ACTIVE INGREDIENTS THEREOF

The invention relates to a composite insect attractant for male white-line dart moths (*Scota segetum*). More particularly, the invention relates to a composition containing a synergistic combination of two active ingredients which can be placed in an insect trap. A still further object of the invention is a process for attracting and trapping white-line dart moths as well as a process for disrupting their mating by air permeation technique. The invention relates further to a novel process for the preparation of 7(Z)-dodecen-1-ol acetate and 9(Z)-tetradecen-1-ol acetate, which are the active ingredients of the composition according to the invention.

White-line dart moth is a widespread pest causing annually recurring damage to almost every cultivated plant, particularly tobacco, sugar beet, other vegetables and cereals. Phosphoric acid esters have been used thus far to combat this pest. These compounds, however, do not have a selective effect, and are also positively toxic to humans. In addition thereto the older caterpillar lives in the earth so that it is practically unaccessible to classical insecticides.

The problems of environmental pollution emerging in connection with the use of conventional pesticide chemicals can be eliminated when compositions containing the natural sex lures (sex pheromones) of the pests to be combatted are used.

Sex pheromones are excreted by the females, and the males of the species can find the females to mate with them by the aid of the characteristic scent of the pheromone.

By putting female moths or pheromone extracted from them into traps, a large number of male moths can be collected and killed in a suitable way, so they are eliminated from the normal cycle of propagation. However the use of pheromones of natural origin is expensive and requires much work; ten thousand or a hundred thousand of female moths obtained from a laboratory breed are necessary to extract a usable amount of active agent. The only method suitable to be applied in agriculture is application of synthetically prepared substances of attractive effect.

Pheromones can be used in plant protection in two ways. According to the first method traps baited with the sex pheromone are used. These traps collect the male moths attracted by the active ingredients. In this way information can be obtained on the appearance of the pest. This method has the advantage over the other forecasting methods utilizing traps that the pheromone-containing traps hive only the preselected pest, whereas light or UV traps hive practically all kinds of insects flying by night. Moreover, the pheromone-containing traps are independent of any source of energy or electric wires. Consequently they can be set out in any part of the given area, so they can indicate the beginning of swarming. This kind of indication is of particular importance in the case of white-line dart moths, because the time of the protection with classical insecticides can be chosen so that it should coincide with the appearance of the young caterpillars. The young larvae do not follow such a hidden course of life as the older ones, and have insecticidal protection is much more effective.

By the aid of the second method, the so-called method of air permeation, the males and females are distorted in finding each other. Thus their mating can be disrupted. In this instance a relatively larger amount of pheromone is emitted into the air over the plant culture to be protected, whereupon the males sense the presence of the pheromone everywhere. The males are thus confused and become unable to find the females. The main advantage of this technique is that extremely selective pheromones-exerting no toxicity against vertebrates and useful arthropoda-are applied in low doses, so the problems of environmental pollutions are eliminated. [Birch, M. C., Ed.: Pheromons, North Holland Publishing Co. London-New York, 1974, p. 495.]

Otto et al. [Arch. Phytopathol. n. Plantenschutz, Berlin, 12, 197-212 (1976)] report on the extraction of the pheromone of white-line dart moth, but they do not disclose the structure of the pheromone.

Now it has been found that when 7(Z)-dodecen-1-ol acetate is combined with 9(Z)-tetradecen-1-ol acetate, a composition with synergistically enhanced effect is obtained which, when used in traps or emitted into the air, produces a strong stimulating reaction on male white-line dart moths.

According to a feature of the present invention there is provided a composite insect attractant for male white-line dart moths (*Scotia segetum*), containing 7(Z)-dodecen-1-ol acetate of the formula I.

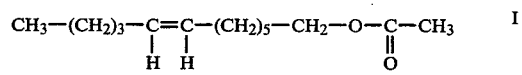

and 9(Z)-tetradecen-1-ol acetate of the formula II

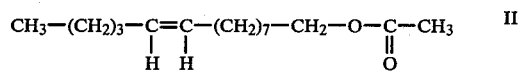

in a weight ratio of (50–90):(50–1) as active ingredients, optionally along with a liquid and/or solid adjuvant.

The new compositions according to the invention contain components I and II preferably in a weight ratio of (70–98):(30–2).

The composition according to the invention can be produced by preparing a solution from the two components in an inert solvent, which solution is then enveloped into capsules or microcapsules. As inert solvents hydrocarbons (e.g. hexane), halogenated hydrocarbons (e.g. dichloromethane), alcohols (e.g. methanol) or ketones (e.g. acetone) can be used. Any organic solvent which is inert toward the components and in which these components are soluble can be used to prepare the solution. The compositions thus-obtained can be preferably used in insect traps. The solvent quickly evaporates out of the trap and the remaining combination of the active agents exerts its attracting effect by gradually evaporating.

To make the evaporation of the active agents even slower, various viscous, non-volatile liquids inert toward the components are preferably added to the composition. For this purpose e.g. sunflower oil, olive oil, paraffin oil, mineral oils, etc. can be used. These liquids do not influence the attractive effect at all, but they keep the speed of the vaporization of the active agents constant, so that the decreasing of the effect occuring otherwise in case of high doses of ingredients as a consequence of the repulsive effect can be avoided.

A composition according to the invention containing 12–67% by weight of sunflower oil, 80–30% by weight of hexane and 8–3% by weight of the combination of the active agents in particularly preferred. An amount of the solution prepared this way providing a dose of the active agents of 0.01–10 mg, preferably of 0.1–3.0 mg is used.

The presence of the viscous liquid is not an obligatory feature in achieving an adequate effect. A further preferred form of the composition according to the invention is a solution containing 50–90% by weight of an inert solvent, preferably hexane or dichloromethane and 50–10% by weight of the active agents, which, applied in a suitable adjuvant (e.g absorbed in a rubber-, caoutchouc- or polyethylene capsule) in an amount providing a dose of the active ingredients of 0.01–10 mg.

According to another feature of the invention there is provided an insect trap for trapping male white-line dart moths (Scotia segetum), as active agent a combination of 7(Z)-dodecen-1-ol acetate of the formula I and 9(Z)-tetradecen-1-ol acetate of the formula II in a weight ratio (50–99):(50–1) in a total amount of 0.01–10.0 mg, preferably 0.1–3.0 mg, optionally dissolved in an inert solvent and/or viscous liquid and/or formulated as a capsule.

According to a further feature of the invention there is provided a process for attracting and trapping male white-line dart moths (Scotia segetum), characterized by exposing said males to the effect of an insect trap containing a combination of 7(Z)-dodecen-1-ol acetate of the formula I and 9(Z)-tetradecen-1-ol acetate of the formula II in a weight ratio of (50–99):(50–1) in a total amount of 0.01–10.0 mg, preferably 0.1–3.0 mg.

The composite insect attractant according to the invention can be permeated in the air to disrupt the mating of the white-line dart moths. The combination of the two active agents is preferably emitted into the atmosphere with a speed of 5.0–30.0 mg/hectare/hour, more preferably 10.0–20.0 mg/hectare/hour.

According to a further feature of the invention there is provided a process for disrupting the mating of white-line dart moths (Scotia segetum), characterized by emitting into the atmosphere a combination of 7(Z)-dodecen-1-ol acetate of the formula I and 9(Z)-tetradecen-1-ol acetate of the formula II in a weight ratio of (50–99):(50–1) with a speed of preferably 5.0–30 mg/hectare/hour, particularly 10.0–20.0 mg/hectare/hour.

According to a still further feature of the invention there is provided a new method for the preparation of the active ingredients of the formulae I and II.

7(Z)-dodecen-1-ol acetate of the formula I was synthetized first by Bestmann et al. [Chem. Ber. 112., 1923 (1979)]. On starting from cycloheptanone an enol ether was formed, then split with ozone in the presence of triphenyl phosphine. The aldehyde ester thus-obtained was converted into ethyl-7(Z)-dodecenoate, reduced and finally acylated. The reaction requires expensive equipment (an ozonator) and runs through circumstantial reaction steps. The reactants are not readily available (e.g. sodium-bis(trimethyl-silyl)amide, triphenyl phosphine.

According to another known method the compound of the formula I is prepared from cyclohexane by a complicated synthesis consisting of 11 reaction steps [J. Ind. Chem. Soc. 55, 589 (1978)]. Owing to the high number of the reaction steps the yield is rather low and the products have to be separated by means of gas chromatography which makes the method uneconomical.

In order to prepare the compound of the formula I, A. S. Kovaileva et al. converted 7-chloro-heptane acid into its phosphonium salt [Zsurnal Org. Kimia 10. 696 (1974)], the phosphonium salt was then reacted with sodium hydride to produce the sodium salt of the triphenyl-5-carboxy-pentylphosphonium-ilyde. The ilyde thus-obtained was reacted with pentanal, the mixture of 7(Z)- and 7(E)-dodecen-acid was first reduced with lithium-aluminum-hydride and finally converted with acetyl chloride into a mixture of 7(Z)-dodecen-1-ol acetate and 7(E)-dodecen-1-ol acetate.

The ilyde-sodium salt formed in the Wittig-step of the synthesis made the reaction mixture, highly polar, which influenced the selectivity of the reaction very disadvantageously. To remove the 5–45% amount of (E)-isomer contained by the end-product an expensive gas-chromatographic process was necessary.

For the preparation of the 9(Z)-tetradecen-1-ol acetate of the formula II Bestmann et al. elaborated two methods. The first started from azelainacid-monoethyl-lester and ran through 8 reaction steps [Chem. Ber. 104, 65 (1971)]. As a consequence of the large number of the steps the yield is low. The starting materials are expensive, so the process is not economical.

According to the other method [Chem. Ber. 108., 3582 (1975)] oleic acid is acetylated, and the acetate was subjected to ozonolysis in the presence of triphenyl phosphine. The 9-acetoxy-nonanal thus-obtained was reacted with an ilyde prepared by treating triphenyl-pentyl-phosphonium salt with potassium dissolved in hexamethyl-phosphoric acid-amide. This method also requires an expensive ozonator which sets limits to its use on industrial scale. Besides, an equivalent amount of the expensive triphenyl phosphine is required, which can not be recovered from the reaction mixture.

According to the novel process of the invention the compound of the formula I is prepared as follows:

7-halogen-heptane-acid-ester of the formula III

$$X-(CH_2)_6-CO_2R \qquad (III)$$

wherein X is a halogen atom and R is $C_{1-4}$ alkyl, is reacted with triphenyl phosphine, preferably in the presence of an acid-binding agent, the compound of the general formula IV thus-obtained,

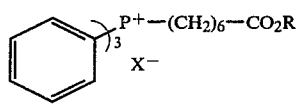

(IV)

wherein X and R have the above defined meanings, is reacted with pentanal in the presence of a suitable base in an organic solvent, the compound of the formula V thus-obtained,

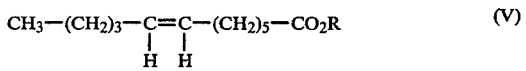
$$CH_3-(CH_2)_3-\underset{H}{C}=\underset{H}{C}-(CH_2)_5-CO_2R \qquad (V)$$

is reduced, the 7(Z)-dodecen-1-ol thus-obtained is acetylated, and, if necessary, the 7(Z)-dodecen-1-ol acetate thus-obtained is isolated from the reaction mixture.

The reaction of the compound of the general formula IV with pentanal is preferably carried out in the presence of sodium hydride or potassium metal in dimethyl-sulfoxide. Bases suitable for Wittig-reactions can be applied as solvents.

The ester of the formula V can be reduced with reducing agents suitable for such reactions, e.g. complex metal hydrides, such as lithium-aluminum hydride, or sodium metal.

The acetylation of the 7(Z)-dodecen-1-ols can be performed by known methods. Acetylchloride or acetic anhydride are preferably used as acylating agents.

9(Z)-Tetradecen-1-ol acetate, the other component of the composition is prepared according to the invention as follows:

9(Z)-octadecen-1-ol acetate is reacted with a mixture of hydrogen peroxide and acetic acid, preferably in a solvent, the 9,10-epoxy-octadecan-1-ol acetate thus obtained is split with periodic acid, the 9-acetoxy-nonanal thus obtained is reacted, in the presence of a base, in an organic solvent, with a compound of the formula VI

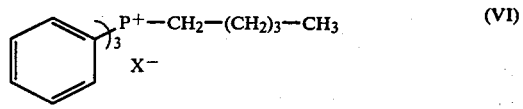

wherein X is halogen, and, if necessary, the 9(Z)-tetradecen-1-ol acetate thus-obtained is isolated from the reaction mixture.

The starting materials of the formula III can be prepared by methods known per se.

The compound of the formula VI can be produced by known methods from triphenyl phosphine and pentyl-halogenide.

9(Z)-octadecen-1-ol acetate can be produced by acetylating 9(Z)-octadecen-1-ol, which is a commercial product.

The processes for the preparation of 7(Z)-dodecen-1-ol acetate and 9(Z)-tetradecen-1-ol acetate according to the invention provide methods consisting of fewer reaction steps and requiring more readily available starting materials and reactants than the known methods. The good selectivity of the Wittig-type synthesis used in the preparation of 7(Z)-dodecen-1-ol acetate makes the purification of the end product unnecessary, nor is there any need to use special and expensive equipment such as an ozonator. Thus the said reactions are suitable for industrial scale production as well.

The effect of the composition according to the invention is illustrated by the following tests Determination of the response produced with 7(Z)-dodecen-1-ol acetate and 9(Z)-tetradecen-1-ol acetate in field tests The traps applied consisted of two plastic sheets of 20×30 cm bent in the form of the top of a tent. The sheets were fixed to one another so that the two tent-shaped crests should be perpendicular to each other. The inside of the lower sheet was smeared with glue to catch the moths flying into the trap. The attractants for the moths were suspended inside the trap at the center of the upper sheet. The traps were situated along a mixed orchard at a height of approximately 1.5 m from the ground at a distance of 25-30 m from each other.

The dose of the attractant was 1 mg. Every fifteenth day the attractant was replaced by a new one. The control traps were not baited. Each treatement was repeated thrice.

The captured moths were collected weekly and their species was identified. The final data were evaluated statistically by the aid of the Duncan's New Multiple Range Test.

The traps baited with 9(Z)-tetradecen-1-ol acetate (II) captured no moths. The 7(Z)-dodecen-1-ol acetate (I) showed a weak attractive effect (on an average of 1.7 moths). The mixtures of the two compounds captured much more male moths. The best result was achieved with the traps containing a mixture of the two compounds of the formula I and II in a ratio of 8:2 (on an average of 20.3 of moths). The mixture containing the components in a ratio of 5:5 captured fewer moths (on an average of 13.0 of moths). The empty control traps captured no male white-line dart moth.

From the above data it follows that, if used alone, the 7(Z)-dodecen-1-ol acetate (I) possesses a weak biological activity. When 9(Z)-tetradecen-1-ol acetate (II) is added, this effect considerably increases. The best attractive effect can be achieved with the mixture containing a greater amount of 7(Z)-dodecen-1-ol acetate and a smaller amount of 9(Z)-tetradecen-1-ol acetate.

TABLE I

| | 7(Z)-dodecen-1-ol acetate (Formula I) | 9(Z)-tetradecen-1-ol acetate (Formula II) | Mixture of components (I) and (II) 8:2 | 5:5 | Control activity |
|---|---|---|---|---|---|
| Number of the male moths captured | 1.7$^a$ | 0.0$^a$ | 20.3$^b$ | 13.0$^b$ | 0.0$^a$ |

$^a$The averages indicated with identical letters do not differ significantly from each other.

The invention is illustrated by the following Examples of non-limiting character:

EXAMPLE 1

12 parts by weight of sunflower oil or paraffin oil, 80 parts by weight of hexane and 8 parts by weight of a mixture of the active ingredients (consisting of 6 parts by weight of the compound of the formula I and 2 parts by weight of the compound of the formula II) are mixed. An amount of the solution thus-obtained corresponding to 1-3 mg of the active ingredient combination is placed into the trap used for forecasting (e.g. blotting up in a rubber capsule or in a polyethylene capillary, admixed to the glues used for hiving moths or absorbing by textile or porous natural or synthetic material).

EXAMPLE 2

One proceeds in the way described in Example 1, with the difference that 10 parts by weight of paraffin oil and 1 part of weight of butyl-hydroxy-toluene and 1 part by weight of anti-fading agent (e.g. Uviron$^R$), 80 parts by weight of hexane and 8 parts by weight of active ingredient are used.

EXAMPLE 3

10 parts by weight of a mixture consisting of 8 parts by weight of the compound of the formula I and 2 parts by weight of a compound of the formula II are admixed to 90 parts by weight of hexane, and amounts of the solution thus-obtained corresponding to 1-2 mg of the active ingredient combination are absorbed into a capillary having a diameter of 0.3 mm and placed into the traps.

EXAMPLE 4

10 parts by weight of a mixture of active ingredients consisting of 7 parts by weight of the compound of the formula I and 3 parts by weight of the compound of the formula II are homogenized with 90 parts by weight of silicone oil and 1-5 mg of the mixture thus obtained is mixed with the glue used in the traps.

EXAMPLE 5

A flannel strip (width=2 cm) is impregnated with a solution prepared as described in Example 3. Hexane is evaporated, and the strip is welded between polyethylene foils. The forms thus-obtained are situated in the area to be protected so that the active ingredient is released into the air in a concentration of 10-30 mg/hour/hectare.

EXAMPLE 6

One proceeds as described in Example 5, with the difference that paraffin oil or odorless kerosene is admixed with the hexane solution so that the ratio of the hexane should be 30-50 parts by weight and the ratio of the paraffin oil or kerosene should be 40-60 parts by weight.

EXAMPLE 7

One proceeds as described in Example 1, with the difference that a mixture of the active ingredients consisting of 4 parts by weight of the compound of the formula I and 4 parts by weight of the compound of the formula II is applied.

EXAMPLE 8

One proceeds as described in Example 1, with the difference that a mixture of the active ingredients consisting of 7.92 parts by weight of the compound of the formula I and 0.08 parts by weight of the compound of the formula II is used.

EXAMPLE 9

Preparation of 5-methoxy-carbonyl-pentyl-triphenyl-phosphonium bromide (Formula IV; X=Br, R=CH$_3$)

A mixture of 30 g (0.134 moles) of 7-bromo-oenanthicmethyl-ester (III; R=CH$_3$, X=Br), 35 g (0.134 moles) of triphenyl phosphine, 0.5 g of dry sodium carbonate and 150 ml of anhydrous acetonitrile is boiled for 30 hours while stirring. The solution is cooled, filtered, and the filtrate is distilled to remove half of the solvent. 200 ml of anhydrous ether are added to the residual solution, the lower phase is separated and washed several times with a total amount of 600 ml of anhydrous ether. The residual gel-like phosphonium salt can be used without any further purification.

Yield: 48 g (73.8%)
NMR /CDCl$_3$/: 1-1.9 /8H, m/, 2.3 /2H, t, J+6 Hz/, 3.4-3.9 /5H, s+m/, 7.3-8 /15H, m/.

Preparation of methyl-[7(Z)-dodecenoate] (Formula V; R=CH$_3$)

A mixture of 2.72 g (0.1 mole) of sodium hydride and 25 ml of anhydrous dimethyl-sulfoxide is stirred under argon at 70° C. until the formation of hydrogen gas is ceased. Then it is cooled to room temperature, a solution of 30 g (0.066 moles) of 5-methoxy-carbonyl-pentyl-triphenyl-phosphonium bromide (Formula IV; R=Br) in 50 ml of anhydrous dimethyl-sulfoxide is added, and the reaction mixture is stirred at 50° C. for half an hour. Thereafter it is cooled to room temperature, stirred with 6.8 g (0.08 moles) of pentanal for 5 hours and allowed to stand over night.

The mixture is poured onto 150 g of broken ice and extracted thrice with a total amount of 300 ml of hexane. The hexane phase is washed with water, dried over magnesium sulfate, the solvent is distilled off and the residue is distilled in vacuo.

Yield: 7.7 g (55%)
B.p: 96°-98° C./0.2 Hgmm
Analysis for C$_{13}$H$_{24}$O$_2$ (212.32): Calculated: C: 73.54%; H: 11.39%; Found: C: 73.82%; H: 11.10%
IR /NaCl/: 1730, 1370, 1240, 1180 cm$^{-1}$
NMR /CCl$_4$/: 0.85 /3H, t, J+6 Hz/, 1-1.6 /10H, m/, 1.7-2.3 /6H, m/, 3.5 /3H, s/, 5.2 /2H, m/.

Preparation of 7(Z)-dodecen-1-ol 0.30 g (0.08 moles) of lithium-aluminum-hydride are added to a solution of 2.0 g (0.01 mole) of methyl-[7(Z)-dodecenoate] (Formula V; R=CH$_3$) in 20 ml of anhydrous ether, and the mixture is refluxed for an hour, under stirring. Then it is cooled, 2 ml of ethylacetate and 10 ml of water are added. The ether phase is separated, the water phase is extracted with 20 ml of ether, the combined ether solutions are washed with water, dried over magnesium sulfate, then the solvent is distilled off.

Yield: 1.46 g (79%)
R$_f$=0.3 /benzene-methanol 5:0.2/
IR /NaCl/: 3380 cm$^{-1}$
NMR /CCl$_4$/: 0.9 /3H, t, J=6 Hz/, 1-1.8 /12 H, m/, 1.85-2.2 /4H, m/, 3.6 /2H, m/, 5.1 /2H, m/.

Characteristic peaks of mass spectrometric analysis: M+ 184 /6/, 167 /2/, 166 /12/, 138 /7/, 124 /7/, 110 /23/, 109 /16/, 96 /35/, 95 /32/, 83 /16/, 82 /54/, 81 /46/, 69 /35/, 68 /36/, 67 /54/, 55 /68/, 54 /32/, 44 /30/, 42 /85/, 31 /100/.

Preparation of 7(Z)-dodecen-1-il acetate (I)

A mixture of 4.0 g of 7(Z)-dodecen-1ol, 12 ml of anhydrous pyridine and 6 ml of acetic anhydride is left to stand at room temperature for 3 hours. Thereafter it is poured onto broken ice, extracted with methylene chloride, the extract is washed with water. Then it is washed with 3 N hydrochloric acid and again with water, and dried over magnesium sulfate, the solvent is distilled off and the residue is distilled in vacuo.

Yield: 4.10 g (83%)
B.p.: 102°-104° C./0.04 mm
IR /NaCl/: 1730, 1360, 1230, 1050 cm$^{-1}$
NMR /CCl$_4$/: 0.85 /3H, t, J=6 Hz/, 1-1.6 /12H, m/, 1.95 /3H, s/, 1.8-2.2 /4H, m/, 3.9 /2H, t, J=6 Hz/, 5.2 /2H, m/.

Characteristic peaks of mass spectrometric analysis: M+ 226 /2/, 198 /4/, 167 /4/, 166 /26/, 156 /9/, 139 /4/, 138 /24/, 137 /5/, 124 /8/, 123 /12/, 111 /6/, 110 /48/, 109 /43/, 99 /7/, 97 /10/, 96 /48/, 95 /62/, 83 /19/, 82 /58/, 81 /54/, 69 /30/, 68 /34/, 67 /59/, 44 /100/, 42 /50/.

EXAMPLE 10

Preparation of 9(Z)-octadecen-1-il acetate

A mixture of 120 ml (102 0.379 moles) of 9(Z)-octadecen-1-ol, 80 ml (86.5 g, 0.85 moles) of acetic anhydride and 80 ml of anhydrous pyridine is allowed to stand at room temperature over a night. Then it is poured onto the mixture of 50 ml of 10% sulfuric acid and 150 g of broken ice and extracted twice with 200 ml of methylene chloride, each. The extract is washed with water, then with saturated sodium-hydrogencarbonate and again with water, dried, then the solvent is distilled off and the residue is distilled in vacuo.

Yield: 104 g (88.3%)

B.p.: 165°–168° C./1 Hgmm; 156° C./0.4 Hgmm

NMR /CCl4/: 0.85 /3H, t, J=6 Hz/, 1.1–1.6 /24H, m/, 2 /3H, s/, 2.05 /4H, m/, 4 /2H, t, J=6 Hz/, 5.3 /2H, m/.

Characteristic peaks of mass spectrometric analysis: M+ 310 /3/, 251 /28/, 250 /70/, 223 /3/, 222 /7/, 195 /3/, 180 /6/, 166 /8/, 152 /14/, 151 /7/, 138 /26/, 137 /20/, 124 /40/, 123 /28/, 111 /20/, 110 /52/, 109 /40/, 97 /46/, 96 /100/, 95 /80/, 83 /60/, 82 /100/, 81 /85/, 70 /16/, 69 /70/, 68 /52/, 67 /85/, 61 /20/, 66 /95/.

Preparation of 9.10-epoxy-octadecan-1-ol acetate

To a solution of 40 g (0.129 moles) of 9(Z)-octadecen-1-il acetate, 0.5 g of sodium acetate, 100 ml of acetic acid and 200 ml of chloroform, 40 ml of 70% hydrogenperoxide are dropwise added, under vigorous stirring. The temperature of the reaction mixture amounts to 35°–40° C. in 10 minutes. The mixture is stirred for six hours, then allowed to stand for a few minutes. The chloroform phase is separated, washed twice with a total amount of 200 ml of distilled water, shaken with 2% sodium sulfite solution, washed again with 100 ml of distilled water, dried and the solvent is distilled off. The residue is distilled off in vacuo.

Yield: 27 g /64.2%/

B.p.: 164°–170° C./0.5 Hgmm

NMR /CCl4/: 0.85 /3H, t, J=6 Hz/, 1–1.8 /28H, m/, 2 /3H, s/, 2.7 /2H, m/, 4 /2H, t, J=6 Hz/.

Characteristic peaks of mass spectrometric analysis: M+ 326 /5/, 252 /6/, 249 /3/, 224 /8/, 213 /20/, 203 /7/, 210 /32/, 199 /3/, 185 /5/, 155 /40/, 154 /5/, 153 /18/, 141 /30/, 140 /10/, 139 /21/, 138 /7/, 137 /6/, 135 /8/, 125 /38/, 124 /68/, 123 /56/, 122 /24/, 113 /8/, 112 /10/, 111 /22/, 110 /12/, 109 /18/, 98 /14/, 97 /42/, 96 /66/, 95 /52/, 84 /20/, 83 /82/, 82 /97/, 81 /88/, 71 /24/, 70 /34/, 69 /100/, 68 /50/, 67 /74/, 61 /58/, 57 /50/, 56 /30/, 55 /98/.

Preparation of 9-acetoxy-nonanal

To a solution of 31 g (0.11 moles) of crystallic periodic acid (HIO4, 2H2O) in 50 ml of water a solution of 25 g (0.076 moles) of 9.10-epoxy-octadecan-1-ol acetate in 220 ml of dioxane is added in 10 minutes. The reaction mixture is stirred at room temperature for a night, then poured onto water. The aqueous suspension is extracted twice with a total amount of 500 ml of petroleum ether, washed with water, dried with magnesium sulfate, the solvent is distilled off, and the residue is distilled in vacuo, under argon. The nonanal forming as a side-product is the first to distille over (b.p.: 80°–85° C., 9.75 g, 90%). The 9-acetoxy-nonanal distils over at 160°–162° C.

Yield: 10.5 g /68.6%/

IR /NaCl/: 1735, 1715, 1360, 1230, 1030 cm−1.

NMR /CCl4/: 1.2–1.9 /12H, m/, 2 /3H, s/, 2.4 /2H, m/, 4 /2H, t, J=6 Hz/, 9.65 /1H, t, J=2 Hz/.

Preparation of 9(Z)-tetradecen-1-il acetate (II)

A mixture of 1.0 g (0.041 moles) of sodium hydride and 20 ml of dry dimethyl sulfoxide is stirred at 70° C., under argon, until the gas-formation is ceased (0.5–1 hour). The reaction mixture is cooled to room temperature, and a solution of 15 g (0.036 moles) of pentyltriphenyl-phosphonium bromide (VI, X=Br) in 35 ml of dry dimethyl sulfoxide is added. The mixture is stirred at 50° C. for half an hour. The red solution obtained is cooled to room temperature, and 5 g (0.025 moles) of 9-acetoxy-nonanal are dropwise added. The mixture is stirred at room temperature for four hours, then allowed to stand over night. Thereafter it is poured onto 150 g of broken ice and extracted trice with a total amount of 300 ml of hexane. The extract is washed with twice distilled water, dried over magnesium sulfate, the solvent is distilled off, and the residue is distilled in vacuo.

Yield: 3 g /47%/

B.p.: 114°–118° C./0.2 Hgmm

IR /NaCl/: 1730, 1360, 1230, 1040 cm−1.

NMR /CCl4/: 0.85 /3H, t, J=6 Hz/, 1–1.6 /16H, m/, 1.95 /3H, s/, 1.85–2.05 /4H, m/, 3.9 /2H, t, J=6 Hz/, 5.2 /2H, m/.

Characteristic peaks of mass spectrometric analysis: M+ 254 /1.5/, 194 /38.4/, 166 /6.3/, 152 /5.6/, 138 /13.3/, 124 /20.5/, 110 /36.8/, 96 /82.6/, 82 /100/.

What we claim is:

1. A composite insect attractant for male white-line dart moths, containing 7(Z)-dodecen-1-ol acetate of the formula I

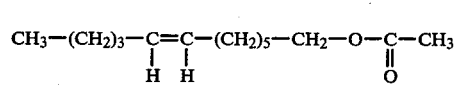

and 9(Z)-tetradecen-1-ol acetate of the formula II

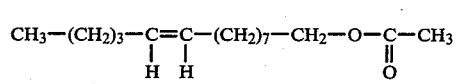

in a weight ratio of 50 to 99:50 to 1 as active ingredients.

2. A composition as claimed in claim 1, which comprises the compounds of the formulae I and II in a weight ratio of 70 to 98:30 to 2.

3. A composition as claimed in claim 1, which further comprises a liquid adjuvant consisting essentially of an inert solvent selected from the group consisting of hydrocarbons, halogenated hydrocarbons, alcohols and ketones and a viscovs non-volatile liquid selected from the group consisting of sunflower oil, olive oil, paraffin oil and mineral oil.

4. A process for disrupting the mating of white-line dart moths, which comprises emitting into the atmosphere a combination of 7(Z)-dodecen-1-ol acetate and 9(Z)-tetradecen-1-ol acetate in a weight ratio of 50 to 99:50 to 1 with a speed of 5.0–30 mg/hectare/hour.

5. A process for attracting and trapping male white-line dart moths which comprises the step of exposing said moths to an insect trap which comprises a sheet smeared with glue and with a combination of 7(Z)-dodecen-1-ol acetate and 9-(Z)-tetradecen-1-ol acetate in a weight ration of 50 to 99:50 to 1 in a total amount of 0.01 to 10.0 mg.

6. The process defined in claim 5 wherein the combination of 7(Z)-dodecen-1-ol acetate and 9-(Z)-tetradecen-1-ol acetate in a weight ration of 50 to 99:50 to 1 is present in a total amount of 0.1 to 3.0 mg.

* * * * *